United States Patent [19]

Runnells

[11] Patent Number: 4,774,063
[45] Date of Patent: Sep. 27, 1988

[54] CONTAINER FOR USE WITH STERILIZERS

[75] Inventor: Robert R. Runnells, Kaysville, Utah

[73] Assignee: MDT Biologic Company, Torrance, Calif.

[21] Appl. No.: 481,080

[22] Filed: Mar. 31, 1983

Related U.S. Application Data

[63] Continuation-in-part of Ser. No. 255,547, Apr. 20, 1981, abandoned.

[51] Int. Cl.$^4$ .................. A61L 2/20; B65D 45/16; B65D 51/16
[52] U.S. Cl. .................. 422/297; 422/292; 422/300; 422/310; 206/45.34; 220/324; 220/366; 220/377
[58] Field of Search .............. 422/292, 297, 300, 310; 206/45.33, 45.34; 220/319, 320, 324, 366, 377

[56] References Cited

U.S. PATENT DOCUMENTS

| | | | |
|---|---|---|---|
| 1,953,765 | 4/1934 | McCluney | 220/377 X |
| 1,956,819 | 5/1934 | Atkins | 206/45.34 X |
| 2,472,028 | 5/1949 | Son | 422/300 X |
| 3,101,864 | 8/1963 | Glickman | 206/45.34 X |
| 3,172,768 | 3/1965 | Joosten et al. | 206/45.34 |
| 3,222,058 | 12/1965 | Beachum | 206/45.34 X |
| 3,454,189 | 7/1969 | Lauterbach | 422/300 X |
| 3,458,275 | 7/1969 | Bense et al. | 422/310 X |
| 3,561,637 | 2/1971 | McConnell | 220/320 |
| 3,676,159 | 7/1972 | Fallowfield | 206/45.34 X |
| 3,741,815 | 6/1973 | Peterson | 220/366 X |
| 3,809,280 | 5/1974 | Park et al. | 220/366 X |
| 3,864,492 | 2/1975 | Fager et al. | 424/283 |
| 3,949,868 | 4/1976 | Allen | 206/45.34 |
| 4,022,324 | 5/1977 | Schuster | 206/439 |
| 4,113,088 | 9/1978 | Binkhorst | 422/292 X |
| 4,135,868 | 1/1979 | Schainholz | 422/300 X |
| 4,196,166 | 4/1980 | Sanderson et al. | 422/300 X |
| 4,228,914 | 10/1980 | Sanderson | 422/310 X |
| 4,229,420 | 10/1980 | Smith et al. | 422/300 X |
| 4,252,268 | 2/1981 | Haire | 220/366 X |
| 4,358,908 | 11/1982 | Song | 220/366 X |
| 4,402,407 | 9/1983 | Maly | 422/300 X |

Primary Examiner—Barry S. Richman
Assistant Examiner—Jill Johnston
Attorney, Agent, or Firm—Trask, Britt & Rossa

[57] ABSTRACT

A container for holding dental or medical implements within the sterilization chamber of a clinical sterilizer includes a bottom tray and a cover element which cooperatively effect a Morton-type closure. The cover element is adapted to permit viewing of the sterilized contents of the container without disturbing the closure. The cover element may be a transparent flexible sheet held against the sidewall of the bottom tray by a clamp, with the sidewall, cover and clamp together effecting the Morton-type closure.

11 Claims, 1 Drawing Sheet

CONTAINER FOR USE WITH STERILIZERS

RELATED PATENT APPLICATIONS

This application is a continuation-in-part to commonly assigned copending application Ser. No. 255,547, filed Apr. 20, 1981, now abandoned, entitled "Sterilizer Tray". The parent application describes and claims a variety of containers with transparent covers which permit viewing the contents of the tray. The present application describes and claims a highly preferred embodiment of the invention disclosed and claimed by the parent application.

BACKGROUND OF THE INVENTION

1. Field

This invention pertains to containers used for the sterilization of dental and medical implements. It specifically provides a container which effects a Morton-type closure, and provides for viewing of the contents of the container without disturbing the closure.

2. State of the Art

Dental and medical implements have generally been sterilized by enclosing them within a rigid covered container, and then exposing the container and its contents to sterilizing conditions. In some instances, the container is provided with openings to permit circulation of chemical vapors, heated air, or steam over the implements within the container. Heretofore, these containers have not permitted the viewing of the contents of the container without subjecting them to nonsterile conditions. Neither have those containers which permit circulation of vapors through the interior been capable of maintaining a sterile environment within the container after its removal from a sterilizer. Typical of conventional containers used with clinical, medical and dental sterilizers are those commonly referred to as "Swedish" trays.

In the field of microbiology, it is often desirable to purge the nonsterile or otherwise undesirable atmosphere from a vial or similar container, replacing it with a biologically inert atmosphere such as nitrogen. Once the desired atmosphere is present in the vial, it is necessary to maintain it during a period of storage. There has evolved a class of closing structures, often embodied as covers or caps, for use with vials or other containers in microbiological procedures. Such structures are known as "Morton" closures. When a Morton-type closure is implaced upon a vial, for example, and the vial is placed in contact with a dynamic source of desired gas (e.g. nitrogen), the desired gas flows through the closure to circulate through the vial, thereby displacing the initial atmosphere from the vial. When the vial is stored in a static ambient atmosphere, the closure serves as an effective barrier against penetration of the ambient atmosphere into the vial. Within the context of this disclosure, the essential characteristics of a Morton-type closure include: (1) suitable access through the closure into and out of the interior of a container to permit the displacement of the initial atmosphere by a desired atmosphere provided to the vicinity of the closure under dynamic flow conditions and (2) sufficient structural protection for that access to contain the desired atmosphere within the container and function as a barrier against penetration by an undesirable ambient atmosphere through the closure under static storage conditions. For example, the closure may consist of an aperture through the vertical sidewall of a container with a physical barrier across the top and spaced slightly in front of the aperture to permit a travel path of vapors in an upward or downward direction with respect to the structure either before or after passing essentially horizontally through the aperture.

Various transparent sheet materials are known to the art. These materials may be provided in flexible form so that they may be conformed to cover objects of varying shapes and sizes. Certain transparent sheet materials are provided in very thin sheets known as films. These films may range from as little as one to a few mils thick. Certain well-known transparent films are marketed under the tradename NYLON. One example of a heat-pervious thermoplastic transparent sheet material is marketed under the tradename designation M&Q Grade 6/6 HS Nylon Flat Sheet by M&Q Plastic Products of Freehold, N.J. Heat-pervious films of this type are impervious to vapors and airborne microorganisms at normal room temperatures, but upon heating become pervious to sterilizing vapors. They are refractory to sterilizing conditions.

SUMMARY OF THE INVENTION

The present invention comprises a container for holding articles during sterilization procedures and thereafter in storage. The sterilization procedures contemplated by this disclosure are those which occur in clinical sized sterilizers of the type which are prevalent in dental or medical offices for routinely sterilizing dental and medical implements such as syringes and hand-held surgical tools.

The container includes a rigid bottom tray formed from a bottom and a continuous wall upstanding from the perimeter of the bottom to define an interior space. Typical dimensions of a bottom tray constructed of heat-resistant plastic or metal would be about six to about eight inches (6–8") wide, about ten to about 12 inches (10–12") long and about one-half to about two inches (½2") in depth. A plurality of trays of this size may conveniently be stacked or otherwise arranged within the interior of a typical clinical or laboratory sized sterilizer.

A cover element adapted to couple with the sidewall of the bottom tray is removably mountable atop the bottom tray to effect a Morton-type closure. The cover element includes a top member adapted to permit viewing of the interior of the container without disturbing the Morton-type closure. For example, the top member may be either wholly or partially transparent. Typically, the cover element includes structure associated with the perimeter of the top member adapted to couple with the sidewall. For example, the cover element may comprise a piece of transparent flexible sheet material, the peripheral portion of which overlaps the sidewall of the bottom tray, being held in place by clamp means.

A Morton-type closure may be effected by an opening through the sidewall of the bottom tray in association with structural means to hold the cover element in overlapping relationship, but out of contact with the opening. Thus, when the container is placed within a chemical sterilizer under sterilizing conditions, sterilizing vapors are permitted to enter into the interior of the bottom tray to displace the initial atmosphere from the tray. When the container is thereafter stored under static ambient conditions, the overlapping cover element provides sufficient barrier against mingling of the ambient atmosphere with the interior's atmosphere to maintain substantially sterile conditions within the interior of the container. In the instance where the bottom tray is substantially rectilinear in configuration as viewed from the bottom; that is, includes two opposed ends and two opposed sidewalls, an opening may be provided in each of the ends. A suitable such opening is configured as a slot through the sidewall at the upper edge of each end; that is, adjacent the top member of the cover element. Referring to the previously described typical container, a suitable slot may be approximately one-eighth inch ($\frac{1}{8}$") deep and approximately three inches (3") in length. A suitable structure for holding the cover element out of contact with the opening is a pair of bosses on the exterior of the end, with the slot running between them. The bosses provide a spacing of the overlapping cover from the slot of about one-sixteenth inch (1/16") to about three-eighths inch ($\frac{3}{8}$").

According to one preferred form of the invention, the clamp means for holding the cover element in position comprises a rigid metal band (for example, a closed loop wire or rod) configured to fit over the sidewall of the bottom tray in a substantially press-fit relationship. Where exterior bosses are provided, the clamp holds the overlapping portion of the cover element in a substantially press-fit relationship with the bosses. Ridges may be provided on the exterior of the sidewall, extending approximately parallel the bottom of the bottom tray. These ridges may be intercooperable with the clamp means to hold the clamp means in position adjacent the sidewall. In the case of a rectilinear tray with apertures and bosses on the ends of the sidewall, the horizontal ridges are preferably located on the longer sides of the sidewall and are adapted so that the clamp must be forced over them, thereby preventing the clamp from rising up over the top edges of the sidewall without the application of deliberate effort.

It is often desirable for the container to include a removable organizing rack means within the interior of the bottom tray. This rack means is adapted to hold in organized fashion a plurality of dental hand instruments, or other sterilizable implements, in approximately parallel side-by-side relationship across substantially the entire cross-sectional area of the bottom tray. Such an organizing device assists in holding the individual implements out of contact with each other and in efficiently distributing them throughout the available tray volume for even and efficient sterilizing contact by steam and/or chemical vapors.

BRIEF DESCRIPTION OF THE DRAWINGS

In the drawings, which illustrate what is presently regarded as the best mode for carrying out the invention.

DESCRIPTION OF THE ILLUSTRATED EMBODIMENT

Figures 1, 2, 3, 4:
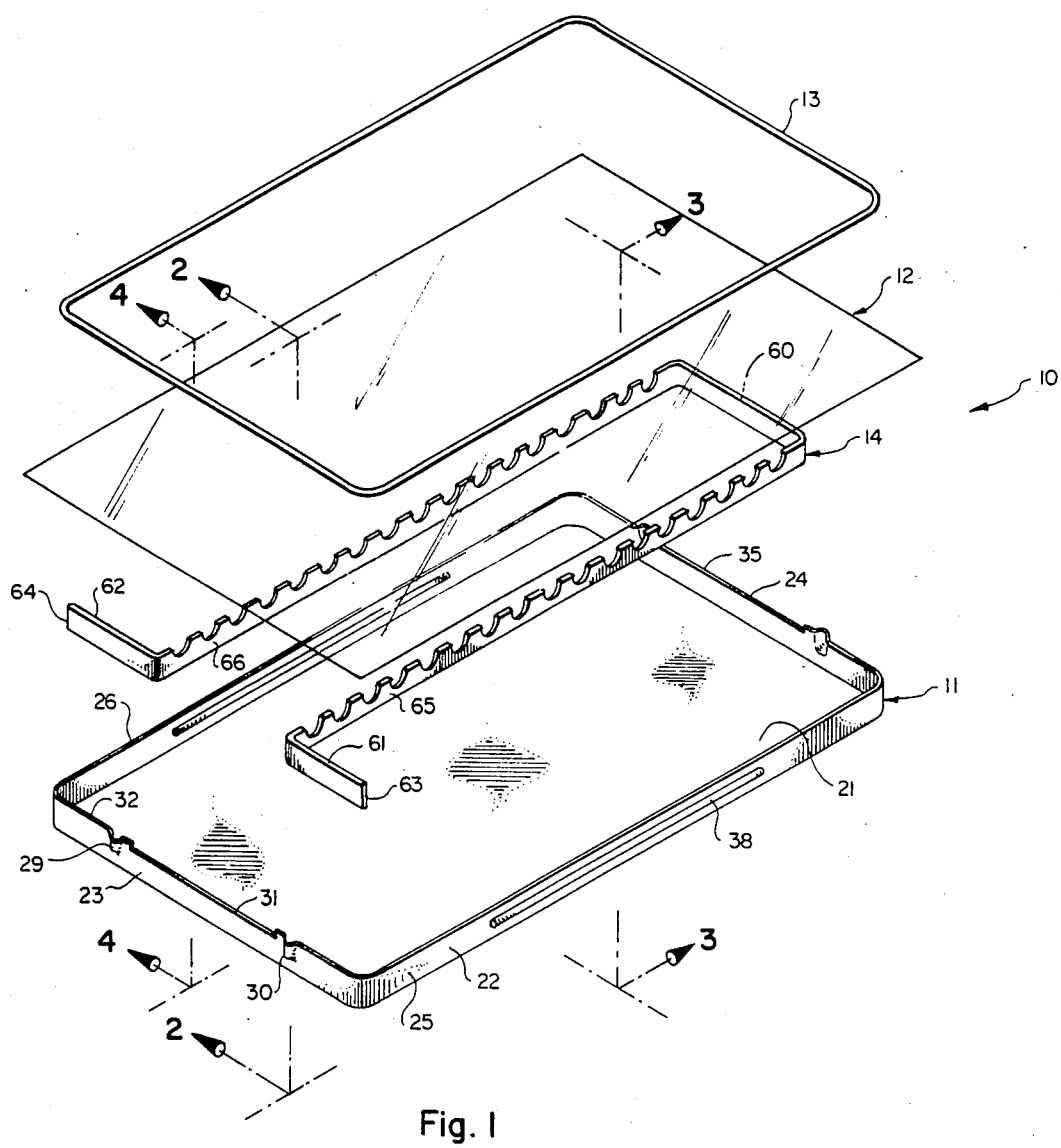
FIG. 1 is an exploded view showing, in perspective, various components of the container of this invention.
FIG. 2 is a fragmentary view in cross-section taken along the reference line 2—2 of FIG. 1, as viewed in the direction of the arrows.
FIG. 3 is a fragmentary view in cross-section taken along the reference line 3—3 of FIG. 1, as viewed in the direction of the arrows.
FIG. 4 is a fragmentary view in cross-section taken along the reference line 4—4 of FIG. 1, as viewed in the direction of the arrows.

Referring to FIG. 1, the illustrated container, designated generally 10, includes a bottom tray, designated generally 11; a cover element, designated generally 12; a clamping band 13 and an organizing rack, designated generally 14.

The bottom tray 11 includes a bottom member 21 with a continuous sidewall 22 upstanding from the perimeter of the bottom 21. In the illustrated instance, the bottom 21 and sidewall 22 are generally rectangular in configuration as viewed from a direction normal the bottom 21. The sidewall 22 thus includes two opposing ends 23, 24 extending between and connecting two opposing sides 25, 26.

Each of the ends 23, 24 carries a pair of external bosses, for example bosses 29, 30 on end 23. A shallow slot 31 extends down from the upper edge 32 of the sidewall 22 between the bosses 29, 30. A corresponding slot 35 is provided in the end 24. Exterior ridges 38 are provided in the sides 25, 26 as shown. Each ridge 38 is approximately parallel the bottom 21. As illustrated, the external bosses 29, 30 extend approximately vertically downward from the upper edge 32 of the sidewall 22 toward the bottom 21. They desirably extend closer to the bottom 21 than the ridge 38 so that when the clamping band 13 is positioned as illustrated in FIGS. 2, 3 and 4 beneath the ridges 38, it is in a substantially press-fit relationship with the bosses 29, 30.

The cover element 12 includes a central top member 40 and a peripheral structure 41 associated with the top 40, adapted to couple with the sidewall 22 as illustrated by FIGS. 2, 3 and 4. In the illustrated instance, the structure 41 is simply the peripheral portion of the cover element 12, which in the illustrated case, comprises a transparent flexible sheet material. The sheet material is selected to withstand sterilizing conditions; that is, it can withstand the temperature and pressures encountered within a sterilizer, and it is also refractory to the atmosphere prevalent in the sterilizer during sterilizing procedures. In any event, the cover element 12 is placed over the top of the tray 11 with its peripheral portion 41 folded around the sidewall 22. The clamping band 13 is pressed over the sidewall 22 to lodge beneath the ridges 38, thereby pressing the peripheral portion 41 against the bosses, e.g. 29, 30. A passageway is thus provided for gas flow, as illustrated by the arrows 50 in FIG. 4, between the sidewall 22 and cover element structure 41, between the bosses 29, 30 into the interior 51 of the container 10. Under dynamic sterilizing conditions, gasses entering the interior 51 in this fashion effectively displace the initial atmosphere from the container 10. After the sterilization cycle is completed, the container 10 may be stored with the cover 12 in place, under static conditions, and the structure 41 effects a sufficient barrier against contamination of the interior of the tray to preserve the sterilized contents in uncontaminated condition for a prolonged period of storage. Of course the dimensions of the bosses 29, 30, slot 31 and interior 51 of the tray 11 are all selected to effect an operable Morton-type closure.

The illustrated organization rack 14 is adapted to fit within the interior 51 of the bottom tray 11. It is dimensioned appropriately to be readily implaced and removed from the interior, but to be securely positioned against disturbance when implaced. That is, the distance between the connecting member 60 and the outwardly projecting leg members 61, 62 is approximately the distance betwen the ends 23, 24, while the distance between the leg ends 63, 64 is approximately the distance between the sides 25, 26. The distance between the leg ends 63, 64 may be slightly greater than the distance of separation between the walls 25, 26 to provide for a mild spring pressure to hold the rack 14 in place. The separation between the rack members 65, 66 is selected to accomodate standard size syringes or other implements, and to support them in evenly spaced, approximately parallel arrangement to make maximum utilization of the entire interior volume of the bottom tray 11. With the rack 14 completely loaded, substantially the entire cross-sectional area of the bottom 21 is occupied. Ordinarily, the separation between the rack members 65, 66 should be somewhat greater than a third of the distance between the sides 25, 26.

Reference herein to details of the illustrated embodiment is not intended to restrict the scope of the apended claims which themselves recite those features regarded as essential to the invention.

DRAWINGS NUMBERING KEY

10—illustrated container, generally
11—bottom tray, generally
12—cover element, generally
13—clamping band
14—organizing rack, generally
21—bottom member
22—continuous sidewall
23—opposing end
24—opposing end
25—opposing side
26—opposing side
29—external boss
30—external boss
31—shallow slot
32—upper edge
35—corresponding slot
38—exterior ridge
40—central top member
41—peripheral structure
50—arrows in FIG. 4
51—interior of the container
60—connecting member
61—outwardly projecting leg member
62—outwardly projecting leg member
63—leg end
64—leg end
65—rack member
66—rack member

I claim:

1. A container for holding articles during sterilization procedures and thereafter in storage comprising:
    a rigid bottom tray with a bottom and a continuous sidewall upstanding from the perimeter of said bottom, thereby to define an interior space; and
    a cover element with a top member and a clamping structure positioned in association with the perimeter of said top member adapted to couple with said sidewall to effect a Morton-type closure of said interior space, said cover element comprising a transparent flexible sheet material which permits viewing of the interior of said container without disturbing said Morton-type closure.

2. A container according to claim 1 including rack means contained within the interior of said bottom tray, for holding a plurality of dental hand instruments in approximately parallel, side-by-side relationship across substantially the entire cross-sectional area of said bottom tray.

3. A container according to claim 1 wherein said cover element comprises a transparent flexible sheet material having a peripheral portion overlapping said sidewall of said bottom tray.

4. A container according to claim 3 wherein said overlapping sheet material is held in place against said sidewall by clamp means.

5. A container according to claim 3 wherein said Morton-type closure is effected by an opening through said sidewall and by structural means associated with said opening to hold said cover element out of contact with said opening so that when the container is placed within a chemical sterilizer under sterilizing conditions, sterilizing vapors are permitted to enter into the interior of said bottom tray, thereby to displace the initial atmosphere from said tray.

6. A container according to claim 5 wherein said sidewall of said bottom tray is rectilinear in configuration as viewed from the bottom, and includes two opposed ends, each of which extends from connection between two opposed sides; and a said opening is provided in each said end.

7. A container according to claim 6 wherein each said opening is postiioned adjacent the top member of said cover element when said cover element is positioned atop said bottom tray.

8. A container for holding articles during sterilization procedures and thereafter in storage conditions, said container comprising:
    a rigid bottom tray having a bottom and a continuous side wall including two opposed ends, each of which extends from connection between two opposed sides, thereby to said bottom tray defining an interior space, said sidewall having an upper edge, each of said ends of said sidewall of said bottom tray being provided with a pari of outwardly extending exterior bosses, said bosses being mounted on an exterior surface of each of said sidewall ends, each said boss having a proximal end and a distal end, each said sidewall defining two slots, each said slot extending from said sidewall upper edge downward toward said bottom, each said slot being positioned between a respective pair of said bosses;
    two exterior ridges, one said ridge being mounted on each of said opposing sides of said bottom tray, each said ridge being oriented approximately parallel said bottom;
    a transparent, flexible sheet positioned over said sidewall's upper edge, said sheet having a peripheral portion overlapping said sidewall of said bottom tray;
    a rigid band positioned over said peripheral portion of said flexible sheet and below said exterior ridges, said ridges retaining said band in a manually detachable locked position over said bosses, said band being positioned between said proximal end and said distal end of each said boss, said band retaining said flexible sheet in a press-fit engagement against said bosses, said bosses constituting structural means for holding said sheet out of contact with said slots, and each said slot being positioned between a pair of said bosses, said sheet defining a cover over said slots and on open pathway between said sheet and said sidewall, said pathway communicating each of said slots with the environment.

9. A container according to claim 8 wherein said sidewall of said bottom tray carries exterior ridges extending approximately parallel the bottom said bottom tray, said ridges being intercooperable with said clamp means.

10. A container according to claim 9 wherein said clamp means comprises a substantially rigid band configurated to slide over said peripheral portion of said transparent sheet material, thereby to hold said peripheral portion in press-fit engagement with said bosses on said ends of said sidewall and in locking engagement with said exterior ridges.

11. A container for holding articles during sterilization procedures and thereafter in storage comprising:

a rigid bottom tray with a rectilinear bottom and a continuous rectilinear sidewall upstanding from a perimeter of said bottom, said sidewall including two opposed ends, each of which extends from connection between two opposed sides, said bottom tray defining an interior space, said sidewall having an upper edge, each of said sidewall ends defining a slot therein which extends from said sidewall upper edge downward toward said bottom, each said sidewall end being provided with a pair of outwardly extending bosses mounted spacedly apart from one another, each said slot being positioned between a respective pair of bosses, each boss having a proximal end and a distal end;

a transparent flexible sheet positioned over said upper edge of said sidewall, said sheet having a peripheral portion overlapping said sidewall of said bottom tray, said sheet coupling with said sidewall to effect a Morton-type closure, wherein said Morton-type closure is effected by each said slot through said sidewall and by each pair of said exterior bosses mounted on said sidewall and associated with a respective said slot to hold said sheet out of contact with said slot so that when the container is placed within a chemical sterilizer under sterilizing conditions, sterilizing vapors under dynamic flow conditions are permitted to enter into the interior of said bottom tray, through an open passageway define between said sheet and said siedwall, thereby to displace the initial atmosphere from said tray;

a pair of exterior ridges mounted on said sidewall sides, each said ridge being oriented approximately parallel said bottom, said flexible sheet having a peripheral portion overlapping said slots and said exterior ridges of said bottom tray;

a clamping structure for retaining said sheet in a manually detachable press-fit relationship against said exterior bosses and out of contact with said slots, said clamping structure having a substantially rigid band positioned over said peripheral portion of said flexible sheet and below said exterior ridges, said ridges retaining said band in a manually detachable locked position over said bosses, said band being positioned over said bosses between said proximal end and said distal end of each said boss, said band being configurated to slide over a peripheral portion of said transparent sheet positioned over said exterior bosses and below said exterior ridges, said flexible sheet providing a transparent window which permit viewing of the interior of said container without disturbing said Morton-type closure;

wherein said slots and said pathway provide a suitable access into and out of said interior space to permit a displacement of an initial atmosphere within said interior space by a desired atmosphere provided to a vicinity of said pathway under dynamic flow conditions; and wherein said flexible sheet provides a sufficient protection for said slots to contain said desired atmosphere within said interior space and further functions as a barrier against penetration by an undesirable ambient atmosphere through said slots under static storage conditions.

* * * * *